United States Patent
Garibaldi et al.

(10) Patent No.: US 7,066,924 B1
(45) Date of Patent: Jun. 27, 2006

(54) METHOD OF AND APPARATUS FOR NAVIGATING MEDICAL DEVICES IN BODY LUMENS BY A GUIDE WIRE WITH A MAGNETIC TIP

(75) Inventors: Jeffrey M. Garibaldi, St. Louis, MO (US); Walter M. Blume, Webster Groves, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1156 days.

(21) Appl. No.: 09/200,055

(22) Filed: Nov. 25, 1998

Related U.S. Application Data (63) Continuation-in-part of application No. PCT/US98/02835, filed on Feb. 17, 1998, and a continuation-in-part of application No. 08/969,165, filed on Nov. 12, 1997, now Pat. No. 5,931,818.

(51) Int. Cl.
*A61M 31/00* (2006.01)
(52) U.S. Cl. .................................. 604/510; 604/164.13
(58) Field of Classification Search .................. 600/11, 600/12, 431, 433, 439, 585; 604/95, 164, 604/270
See application file for complete search history.

(56) References Cited

U.S. PATENT DOCUMENTS

| | | | |
|---|---|---|---|
| 4,244,362 A * | 1/1981 | Anderson | 604/95 |
| 4,671,287 A | 6/1987 | Fiddian-Green | |
| 5,431,640 A * | 7/1995 | Gabriel | 604/270 |
| 5,464,023 A * | 11/1995 | Viera | 604/95 |
| 5,622,169 A * | 4/1997 | Golden et al. | 600/424 |
| 5,623,943 A | 4/1997 | Hackett et al. | |
| 5,630,427 A | 5/1997 | Hastings | |
| 5,636,644 A | 6/1997 | Hart et al. | |
| 5,647,843 A | 7/1997 | Mesrobian et al. | |
| 5,706,827 A | 1/1998 | Ehr et al. | |
| 5,902,238 A * | 5/1999 | Golden et al. | 600/424 |
| 5,931,818 A * | 8/1999 | Werp et al. | |

* cited by examiner

*Primary Examiner*—Nicholas Lucchesi
*Assistant Examiner*—Aamer Ahmed
(74) *Attorney, Agent, or Firm*—Harness Dickey & Pierce PLC (57) ABSTRACT

A guide wire combined with a catheter or medical device for moving through a body lumen to a desired position in the body with the aid of an applied magnetic field. The guide wire is provided with a magnet on its distal end that can be oriented or oriented and moved by the application of a magnetic field to the magnet. A catheter or other medical device can be advanced over the guide wire. Once the medical device is in its desired position, the magnet can be withdrawn through the lumen of the catheter. Alternatively, a guide wire with a magnet on its distal end can be docked at the distal end of a catheter or medical device and can be oriented, or oriented and moved by the application of a magnetic field.

14 Claims, 6 Drawing Sheets

METHOD OF AND APPARATUS FOR NAVIGATING MEDICAL DEVICES IN BODY LUMENS BY A GUIDE WIRE WITH A MAGNETIC TIP

CROSS REFERENCE TO RELATED APPLICATION

This application is a continuation in part of PCT application Ser. No. PCT/US98/02835 filed Feb. 17, 1998 and is a continuation in part of U.S. application Ser. No. 08/969,165 filed Nov. 12, 1997 and issued Aug. 3, 1999 as U.S. Pat. No. 5,931,818.

FIELD OF THE INVENTION

This invention relates to a method of, and apparatus for, navigating medical devices in body lumens, such as in blood vessels, the trachea, the gastrointestinal tract, or the urinary tract.

BACKGROUND OF THE INVENTION

Many diagnostic and therapeutic medical procedures require navigating a medical device to a particular location through lumens in the body. For example, procedures such as cardiac catheterizations and interventional neuroradiology procedures involve the introduction of medical devices through the arteries; bronchoscopies involve the introduction of medical devices through the trachea; endoscopies and colonoscopies involve the introduction of instruments through the gastrointestinal tract; and urethroscopies involve the introduction of medical devices through the urinary tract.

Numerous methods and apparatus have been developed for introducing medical devices in the body. Many of these methods employ guide wires for remotely controlling the orientation of the tip of the medical device as it is advanced in the body lumen. These guide wires typically have a bend in their distal ends, the tip is rotated until the tip is properly oriented, and the wire is then advanced. It is a difficult and tedious process to steer a medical device remotely with a guide wire since the orientation of the guide wire is difficult to control. Thus, these procedures can be prolonged, which increases the risk to the patient and fatigues the physician.

It has been proposed to guide medical devices in the body with magnets, see Yodh, Pierce, Weggel, and Montgomery, A New Magnetic System, for 'Intravascular Navigation', Medical & Biological Engineering, Vol. 6, No. 2, pp. 143–147 (March 1968), incorporated herein by reference. This article proposes a magnetically tipped catheter that is steered within the body by an externally applied magnetic field. However, the magnet in this proposed device is attached to the catheter which can impair the ability to control the magnet. Moreover, there is no provision for removing the magnet and leaving the catheter or other medical device in place. Thus, only one such catheter can be directed to a given position because the magnetic field acting on one magnet will also act on the other magnets in the vicinity.

SUMMARY OF THE INVENTION

The methods and apparatuses of the present invention involve magnetically guiding a medical device through a lumen in the body. Generally, according to the method of this invention, a magnet is provided on the end of a guide wire and an externally applied magnetic field orients the magnet in the body lumen. The magnet can be advanced through the body lumen by manipulating the magnetic field or by pushing the guide wire.

According to a first embodiment of this invention, a catheter may be disposed over a guide wire having a magnet on its distal end. The guide wire and catheter combination is introduced into a body lumen through a natural or surgically formed opening. Once in the body the guide wire and catheter combination is navigated through the body lumen by applying a magnetic field, which acts on the distal end of the guide wire, orienting it. Typically, the guide wire is advanced slightly ahead of the catheter at a branch in the body lumen, and a magnetic field is applied to orient the tip of the guide wire, and the guide wire is advanced in the direction of the tip which is oriented into the selected branch. The guide wire can be advanced by the application of the magnetic field, by pushing at the proximal end, or by both. The catheter is then advanced over the guide wire. This process is repeated until the distal end of the catheter is at its desired location. Once the distal end of the catheter is in the desired position, the magnet can be withdrawn through the lumen of the catheter by pulling on the tether. Treatment, such as drug therapy or embolizing agents, can then be passed through the catheter.

According to a second embodiment of this invention, a guide wire with a magnet on the tip may be docked at the distal end of the lumen inside a catheter or other medical device. The guide wire and catheter combination is introduced into a body lumen through a natural or surgically formed opening. Once in the body lumen, the guide wire and catheter combination is navigated through the body lumen by applying a magnetic field, which acts upon the magnet-tipped guide wire in the catheter, orienting it. The catheter is advanced by pushing the guide wire. Once the distal end of the catheter is in the desired location, the guide wire can be withdrawn through the lumen of the catheter by pulling on the guide wire. Treatment, such as drug therapy or embolizing agents, can then be passed through the catheter.

The methods of the various embodiments of this invention, and the guide wire of the various embodiments of this invention, facilitate quick, easy and accurate positioning of a catheter or other medical device via a body lumen. Once the catheter is properly positioned, it can be used during a diagnostic or therapeutic procedure, either directly or as a passage for other medical devices.

These and other features and advantages will be in part apparent and in part pointed out hereinafter.

BRIEF DESCRIPTION OF THE DRAWINGS

Corresponding reference numbers indicate corresponding parts throughout the several views of the drawings.

DETAILED DESCRIPTION OF THE PREFERRED EMBODIMENTS

Figure 1:
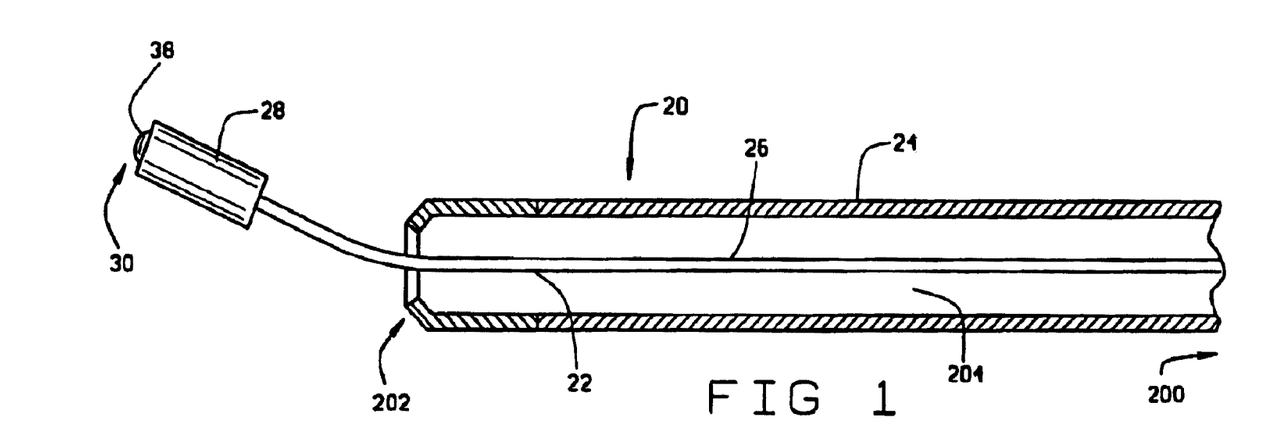
FIG. 1 is a longitudinal cross-sectional view of a guide wire and catheter combination constructed according to the principles of a first embodiment this invention.

A guide wire and magnet combination constructed according to the principles of a first embodiment of this invention is indicated generally as 20 in FIG. 1. The guide wire and catheter combination 20 comprises a guide wire 22 and a catheter 24. The guide wire 22 comprises a wire 26, which is preferably made of nitinol, which is highly flexible and resists kinking, although the guide wire could be made of some other suitable material. A magnet 28 is mounted on the distal end 30 of the wire 26. This magnet may either be a permanent magnet or a permeable magnetic material. A permanent magnet is easier to orient under the application of a magnetic field, as described below, but a permeable magnetic material is easier to pull under the application of a magnetic field.

In the preferred embodiment, the magnet 28 is made of NdFeB (neodymium-iron-boron) or samarium cobalt and is sized to respond to the magnetic field that will be applied to orient the guide wire 22 in the body lumen and to be retracted through the catheter 24. The magnet 28 is preferably elongate so that it can orient the tip of the guide wire 22 in the presence of an applied magnetic field. Magnets of about 0.3 mm (0.02 inches) to about 0.7 mm (0.03 inches) in diameter, and about 1 mm (0.04 inches) to 1.5 mm (0.06 inches) long are sufficiently large for use in navigating a guide wire.

Figure 2:
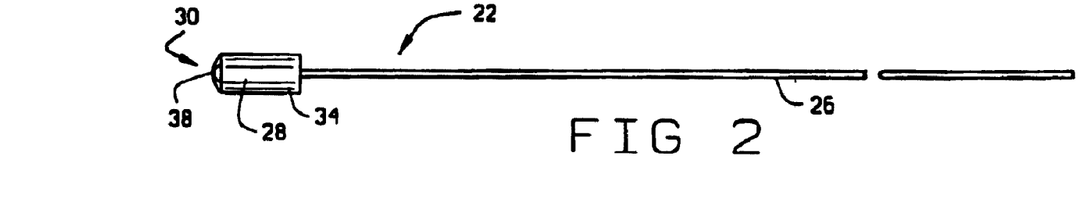
FIG. 2 is a plan view of the guide wire of the first embodiment.
Figure 3:
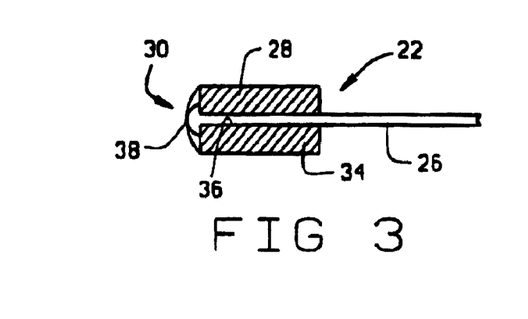
FIG. 3 is an enlarged cross-sectional view of the distal tip of the guide wire.

As shown in FIGS. 2 and 3, the magnet 28 is preferably a cylindrical body 34 with an axial bore 36 therethrough. The distal end of the wire 26 extends through the bore 36, and is secured with a bead 38 of adhesive on the distal side of the magnet 28. The bead 38 also provides a rounded head on the distal end 30 of the guide wire 22.

Figure 4:
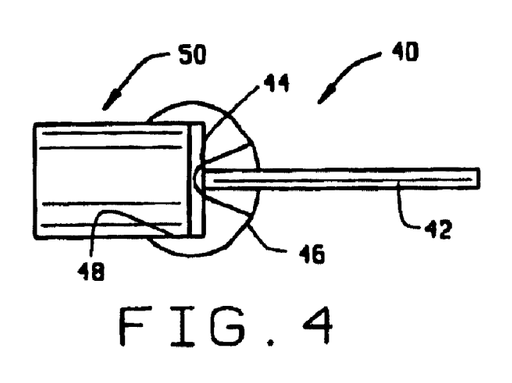
FIG. 4 is an enlarged cross sectional view the distal end of a first alternate construction of the guide wire of the first embodiment, using a socket to secure the magnet.

A first alternate construction of the guide wire 22 of the first embodiment is indicated generally as 40 in FIG. 4. The guide wire 40 is similar in construction to guide wire 22, comprising wire 42, having a proximal end (not shown) and a distal end 44. A mounting body 46, having a socket 48 therein, is attached to the distal end 44 of the wire. A magnet 50 is mounted in the mounting body. The magnet can be secured in the mounting body with adhesive, or the socket 48 can be crimped to secure the proximal end of the magnet 50 in the socket 48.

Figure 5:
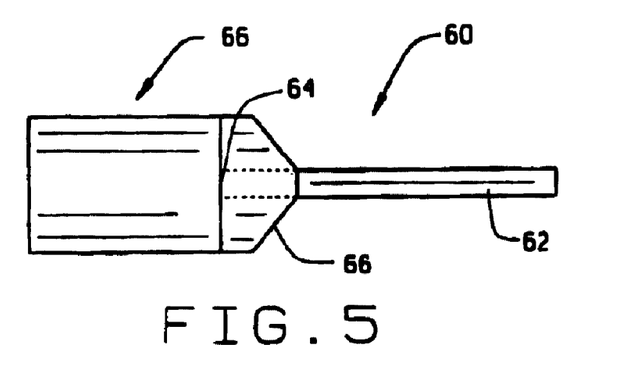
FIG. 5 is an enlarged cross sectional view of the distal end of a second alternate construction of the guide wire of the first embodiment, using a collar to secure the magnet.

A second alternate construction of the guide wire 22 of the first embodiment is indicated generally as 60 in FIG. 5. The guide wire 60 is similar in construction to guide 22, comprising a wire 62 having a proximal end (not shown) and a distal end 64. A mounting collar 66 is attached to the distal end 64 of the wire 62. A magnet 68 is mounted on the mounting collar 66. The magnet 68 can be secured to the mounting collar 66 by adhesive or by fusion.

Figure 6:
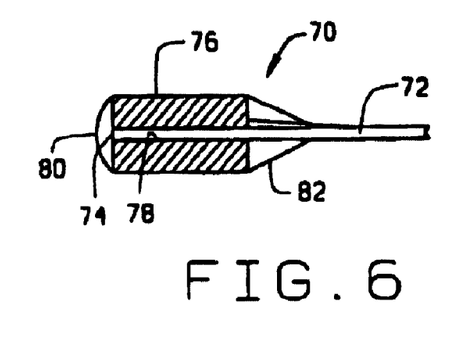
FIG. 6 is an enlarged cross-sectional view of a third alternate construction of the distal section of the guide wire.

A third alternate construction of the guide wire 22 is indicated generally as 70 in FIG. 6. The guide wire 70 is similar in construction to guide 22, comprising a wire 72 having a proximal end (not shown) and a distal end 74, and a magnet 76 mounted on the distal end of the wire 72. The magnet 76 is preferably a cylindrical body with an axial bore 78 therethrough. The distal end of the wire 24 extends through the bore 78, and is secured with a bead 80 of adhesive on the distal side of the magnet 76. The bead 80 also provides a rounded head on the distal end of the guide wire 22. There is a tapering collar 82 on the wire 26 proximal to the magnet 76. The collar 82 facilitates withdrawing the magnet 76 through the distal end of the catheter 24. The collar can be made of platinum or some other non-magnetic radio opaque material so that the position of the end of the guide wire can be easily located with x-ray or fluoroscopic imaging equipment.

Figure 7:
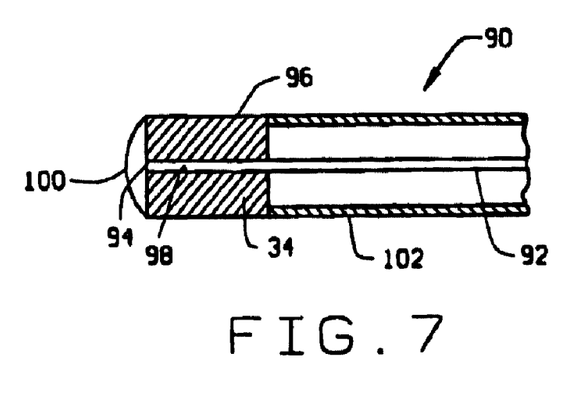
FIG. 7 is an enlarged cross-sectional view of a fourth alternate construction of the distal section of the guide wire.

A fourth alternative construction of a guide wire 22 is indicated generally as 90 in FIG. 7. The guide wire 90 is similar in construction to guide wire 22, comprising a wire 92 having a proximal end (not shown) and a distal end 94, and a magnet 96 on the distal end of the wire 92. The magnet 96 is preferably a cylindrical body with an axial bore 98 therethrough. The distal end of the wire 24 extends through the bore 98, and is secured with a bead 100 of adhesive on the distal side of the magnet 96. The bead 100 also provides a rounded head on the distal end of the guide wire 90. The guide wire 90 includes a sheath 102, made of flexible polyurethane tubing, extending over the wire 92. The sheath 102 preferably has the same outside diameter as the magnet 96, to smoothly slide in the lumen of the catheter, and to help prevent excessive movement of the guide wire 90 within the lumen. The sheath 102 is preferably secured to the proximal end of the magnet 96 with an adhesive, such as SICOMET 40 available from Tracon.

Figure 8:
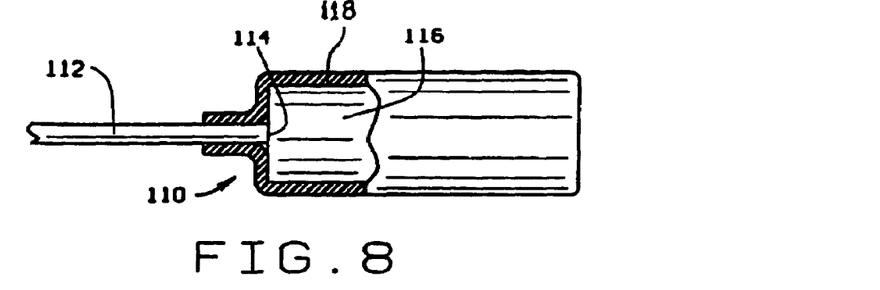
FIG. 8 is a side elevation view of the distal section of a fifth alternate construction of the guide wire of the first embodiment with a portion broken away to show details of the construction.

A fifth alternate construction of the guide wire of the first embodiment is indicated generally as 110 in FIG. 8. Guide wire 110 comprises a wire 112 having a proximal end (not shown) and a distal end 114. The wire 112 is preferably made of nitinol, which is highly flexible and resists kinking, although it could be made of some other suitable material. A magnet 116, which can either be a permeable magnet or a permanent magnet, is secured on the distal end 114. A permanent magnet is easier to orient under the application of a magnetic field, as described below, but a permeable magnetic material is easier to pull under the application of a magnetic field.

The magnet 116 is preferably made of NdFeB (neodymium-iron-boron) or samarium cobalt and is sized to respond to the magnetic field that will be applied to orient the distal tip of the guide wire 110 in the body lumen and to be retracted through the lumen of the catheter or other medical device. The magnet 116 is preferably elongate so that it can orient the distal tip of the guide wire 110 in the presence of an applied magnetic field. Magnets of about 0.3 mm (0.02 inches) to about 0.7 mm (0.03 inches) in diameter, and about 1 mm (0.04 inches) to 1.5 mm (0.06 inches) long are sufficiently large for use in navigating a guide wire.

As shown in FIG. 8, the magnet 116 is preferably a cylindrical body. A magnetic or non-magnetic sleeve 118, made of a suitable sheet material or wire, covers the magnet 116 and extends over the distal end 114 of the guide wire 110, securing the magnet on the wire. In this preferred embodiment shown in FIG. 8 the sleeve 118 is made from a thin plastic tube, which is can be secured over the magnet and the distal end of the guide wire, with an adhesive, or more preferably, by heat shrinking.

Figure 9:
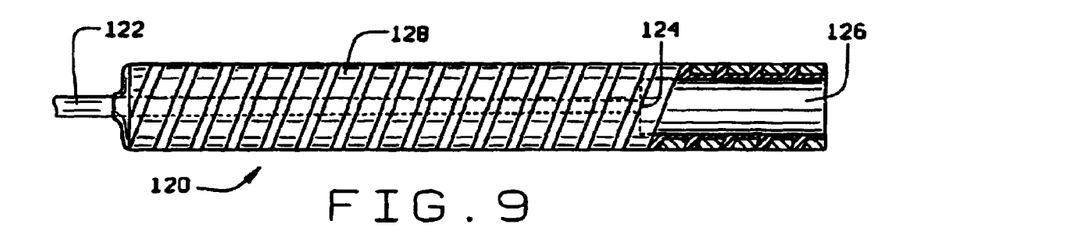
FIG. 9 is a side elevation view of the distal end section of a sixth alternate construction of the guide wire of the first embodiment.

A sixth alternate construction of the guide wire of the first embodiment is indicated generally as 120 in FIG. 9. Guide wire 120 comprises a wire 122 having a proximal end (not shown) and a distal end 124. The wire 122 is preferably made of nitinol, which is highly flexible and resists kinking, although it could be made of some other suitable material. A magnet 126, which can either be a permeable magnet or a permanent magnet, is secured on the distal end 124, for example with adhesive. A permanent magnet is easier to orient under the application of a magnetic field, as described below, but a permeable magnetic material is easier to pull under the application of a magnetic field.

The magnet 126 is preferably made of NdFeB (neodymium-iron-boron) or samarium cobalt and is sized to respond to the magnetic field that will be applied to orient the distal tip guide wire 120 in the body lumen and to be retracted through the lumen of the catheter or other medical device. The magnet 126 is preferably elongate so that it can orient the distal tip of the guide wire 120 in the presence of an applied magnetic field. Magnets of about 0.3 mm (0.02 inches) to about 0.7 mm (0.03 inches) in diameter, and about 1 mm (0.04 inches) to 1.5 mm (0.06 inches) long are sufficiently large for use in navigating a guide wire.

As shown in FIG. 9, the magnet 126 is preferably a cylindrical body. A sleeve 128, made of wire, covers the magnet 126 and extends over the distal end 124 of the wire 122, helping to secure the magnet on the wire. In this preferred embodiment shown in FIG. 9, the sleeve 128 is a coil of platinum wire, the proximal end of which is secured to the wire 122 proximal to the distal end 124, and the distal end of which is secured to the magnet 126. The coil improves the axial stiffness of the distal end while leaving the guide wire flexible in other directions to permit magnetic navigation. The coil also improves the radiopacity of the end of the guide wire so that it can be seen on x-ray and fluoroscopic images. The coil is secured to the wire 122 and to the magnet 126 with adhesive. The adhesive preferably fills the spaces between the turns of the coil around the magnet 126, so that the surface is smooth.

Figure 10:
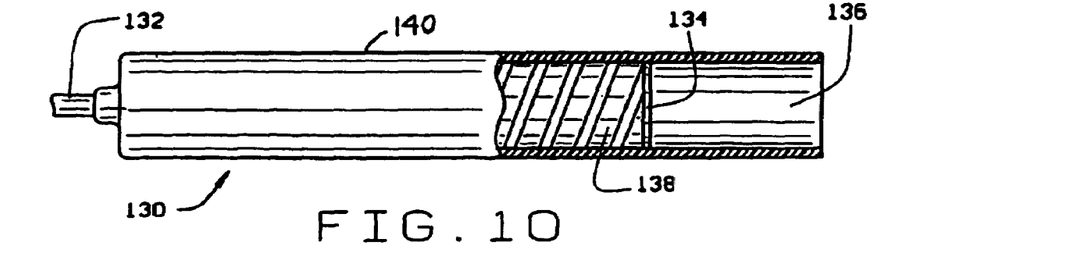
FIG. 10 is a side elevation view of the distal end section of a seventh alternate construction of the guide wire of the first embodiment.

A seventh alternate construction of the guide wire of the first embodiment is indicated generally as 130 in FIG. 10. Guide wire 130 comprises a wire 132 having a proximal end (not shown) and a distal end 134. The wire 132 is preferably made of nitinol, which is highly flexible and resists kinking, although it could be made of some other suitable material. A magnet 136, which can either be a permeable magnet or a permanent magnet, is secured on the distal end 132, for example with adhesive. A permanent magnet is easier to orient under the application of a magnetic field, as described below, but a permeable magnetic material is easier to pull under the application of a magnetic field.

The magnet 136 is preferably made of NdFeB (neodymium-iron-boron) or samarium cobalt and is sized to respond to the magnetic field that will be applied to orient the distal tip guide wire 130 in the body lumen and to be retracted through the lumen of the catheter or other medical device. The magnet 136 is preferably elongate so that it can orient the distal tip of the guide wire 130 in the presence of an applied magnetic field. Magnets of about 0.3 mm (0.02 inches) to about 0.7 mm (0.03 inches) in diameter, and about 1 mm (0.04 inches) to 1.5 mm (0.06 inches) long are sufficiently large for use in navigating a guide wire.

As shown in FIG. 10, the magnet 136 is preferably a cylindrical body. A coil 138 of platinum wire is disposed over the distal end portion of the wire 132. The proximal end of the coil is attached to the wire 132 proximal to the distal end, and the distal end of the coil is attached to the proximal end of the magnet 136. The coil improves the axial stiffness of the distal end while leaving the guide wire flexible in other directions to permit magnetic navigation. The coil also improves the radiopacity of the end of the guide wire so that it can be seen on x-ray and fluoroscopic images. The coil 98 is secured to the wire 92 and to the magnet 96 with adhesive. A sleeve 140 covers the magnet 136 and extends over the coil 138 and the distal end 134 of the wire 130, helping to secure the magnet and the coil on the wire. In this preferred embodiment shown in FIG. 10, the sleeve 140 is a tube of a flexible plastic material, that is secured with an adhesive, or more preferably by heat shrinking.

Figure 11:
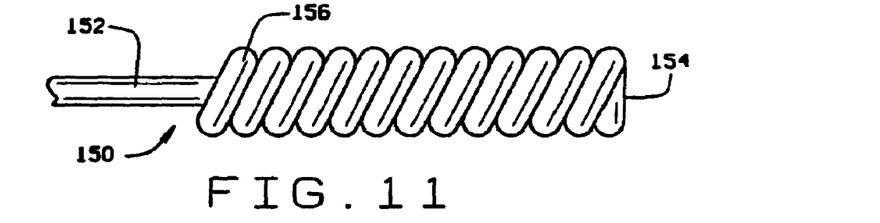
FIG. 11 is a side elevation view of the distal section of an eighth alternate construction of the guide wire of the first embodiment.
Figure 11A:
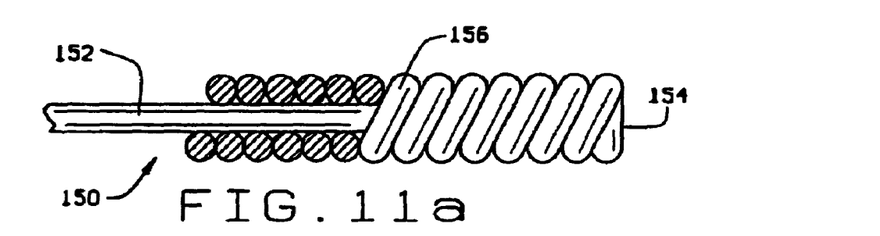
FIG. 11a is an enlarged side elevation view of the eighth alternate construction of the distal end section, with a portion broken away to show details of the construction.

An eighth alternate construction of the guide wire of the first embodiment is indicated generally as 150 in FIGS. 11 and 11a. Guide wire 150 comprises a wire 152, having a proximal end (not shown) and a distal end 154. The wire 152 is preferably made of nitinol, which is highly flexible and resists kinking, although it could be made of some other suitable material. The wire 152 tapers toward the distal end 154. The portion of the wire 152 adjacent the distal end is surrounded by a magnetic coil 156.

Figures 12, 12A:
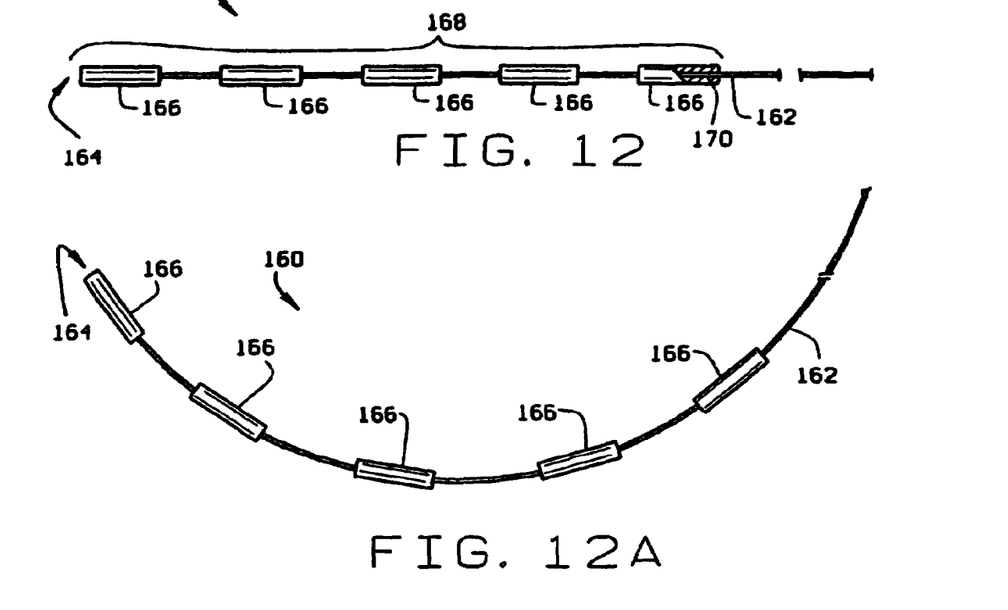
FIG. 12 is a side elevation view of the distal section of a ninth alternate construction of the guide wire of the first embodiment.
FIG. 12a is a side elevation view of the distal section of the ninth alternate construction of the guide wire, in a magnetic field.

A ninth alternate construction of the first embodiment of a guide wire according to the principles of this invention is indicated generally as 160 in FIGS. 12 and 12a. Guide wire 160 comprises a wire 162 having a proximal end (not shown) and a distal end 164. Instead of a single magnet on the distal end of the wire, as in the first embodiment, guide wire 160 has a series of spaced magnets 166 on the distal end portion 168 of the wire 162. The magnets 166 each preferably have a generally cylindrical body, with an axial bore 170 extending therethrough. The distal portion 54 of the wire 56 extends through the bores 60, and the magnets 52 are secured to the wire 56 in spaced apart relation with adhesive.

The magnets 166 are preferably made from NdFeB, and have a diameter of 2 mm (0.08 inches) and are 4 mm (0.16 inches) long. The magnets 166 are preferably spaced over the distal 5 cm (2 inches) of the guide wire 160, and are spaced 1 cm (0.4 inches) on center. Of course some other size magnets and/or different magnet spacing could be used.

Moreover the spacing of the magnets does not have to be equal. This third alternate construction is particularly useful for an electrophysiology catheter where the magnetic fields could pull or shape the guide wire 160 to the heart wall, thereby guiding the electrophysiology catheter over the guide wire against the heart wall.

As shown in FIG. 12a, upon the application of a magnetic field, the magnets 166 on the distal end portion 164 of the guide wire 160 cause the guide wire to assume a particular shape dictated by the field. Thus by controlling the applied magnetic field, the shape of the distal portion of the guide wire can be controlled, facilitating the navigation through, or shaping to, the body lumen. The guide wire 160 can be advanced by pulling with a magnetic force on the magnets 166, or the proximal end can be manually pushed. A magnetic pulling force could also be used to hold the catheter with guide wire to the wall of a body lumen.

Figure 13:
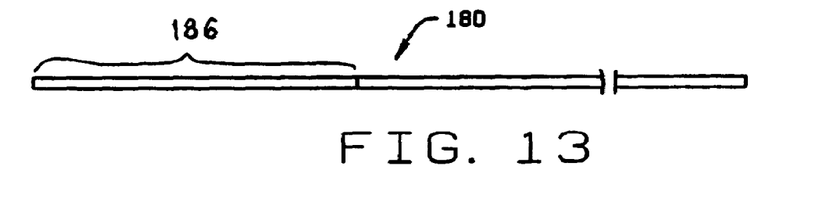
FIG. 13 is a side elevation view of a tenth alternate construction of the distal section of the guide wire.
Figure 13A:
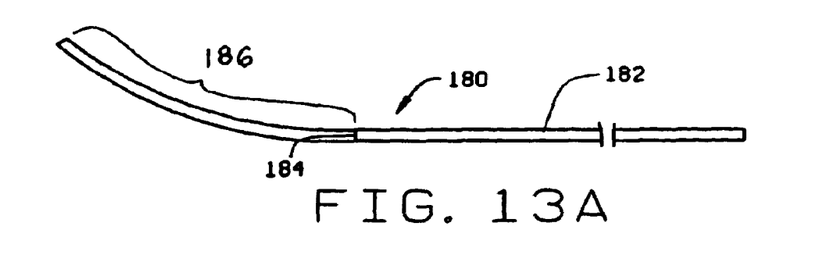
FIG. 13a is a side elevation view of a tenth alternate construction of the distal tip of the guide wire, in a magnetic field.

A tenth alternate construction of the first embodiment of a guide wire constructed according to the principles of the present invention is indicated generally as 180 in FIGS. 13 and 13a. The guide wire 180 comprises a wire 182, having a proximal end (not shown) and a distal end 184. Instead of the single magnet on the distal end of the wire, or a plurality of magnets on the distal end portion of the wire, the distal end portion 186 of guide wire 180 is made from a flexible magnetic material.

The distal end portion 186 is preferably about 0.25 mm (0.01 inches) in diameter, and about 1 cm (0.4 inches) long. The distal end portion can be made of a permeable magnetic material such as a steel or a magnetic stainless steel wire, or a steel or a magnetic stainless steel braid.

As shown in FIG. 13a, upon the application of a magnetic field, the distal end portion 186 of the guide wire 180 assumes a particular orientation dictated by the field. Thus by controlling the applied magnetic field, the orientation and/or shape of the distal portion 186 of the guide wire 180 can be controlled, facilitating the navigation through the body lumen. The guide wire 180 can be advanced by magnet force on the distal end portion 186, or the proximal end can be pushed. The magnetic field can also function to selectively stiffen the distal end portion 186 of the guide wire, to facilitate navigation through the body lumen. This allows the guide wire 182 to be designed with the minimum amount of stiffness to overcome static friction when applying an axial pushing force on at the proximal end. Sufficient stiffness for navigation can be provided by applying a magnetic field to the distal tip.

As shown in FIG. 1, the catheter 24 is preferably of conventional construction, having a proximal end 200, a distal end 202, and a lumen 204 extending therebetween. The catheter 24 can be made of polyurethane tubing, or some other suitable material. The size of the catheter 24 depends upon where in the body it will be introduced, and how it will be used. For example, for use in the blood vessels in the brain, the catheter might have an outside diameter of about 0.7 mm (0.03 inches), an inside diameter of about 0.6 mm (0.02 inches), and a length of about 2 m (6.6 feet). Of course, medical devices other than catheters can be used with the guide wire, for example an endoscope where the guide wire is inserted through its working channel. These devices would typically include a lumen extending all or partly along the length of the device that passes over the guide wire so that the device follows the guide wire.

One of the guide wires of the present invention can be introduced into a body lumen, such as a blood vessel, and navigated to its desired location by the controlled application of magnetic fields. The application of a magnetic field allows the operator to steer the distal end of the guide wire by orienting the distal end of the guide wire to the desired direction of travel. The guide wire can be advanced using the magnetic field to pull the magnet on the distal end of the guide wire, or the guide wire can be advanced by pushing the proximal end. As the guide wire advances, the catheter 24 or other medical device can be advanced over the guide wire, until the catheter or medical device is in its desired location.

Once the distal end 202 of the catheter 24 has been placed in its desired location, the guide wire can be left in place, or if the magnet is sufficiently small, the guide wire can be withdrawn through the lumen 204 of the catheter and out the proximal end 200.

The magnetic articulation of the distal end of the guide wire eliminates the need to provide a permanent bend in the guide wire in order to navigate through branches in body lumens. The straight configuration of the guide wires permitted by the present invention permits faster and easier navigation in straight sections of the body lumen and reduces unintentional diversion down branches of the lumen.

Figure 14:
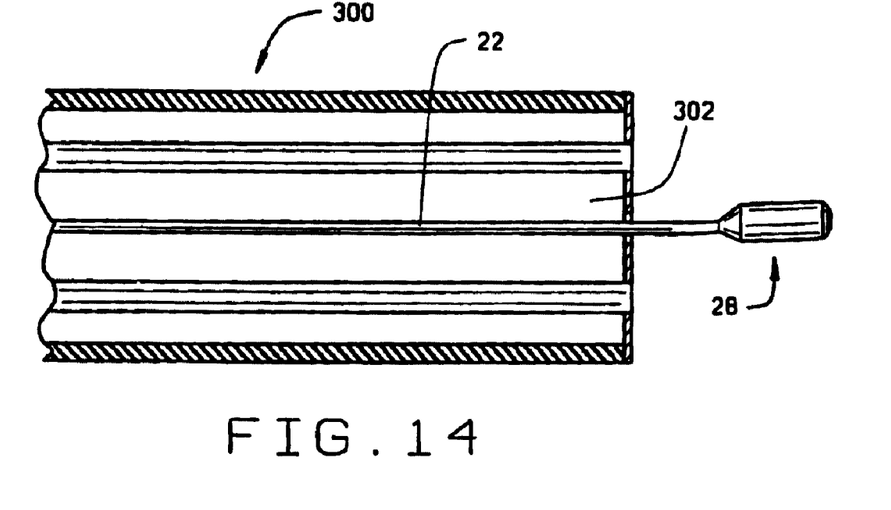
FIG. 14 is a longitudinal cross-sectional view of the guide wire and endoscope combination constructed according to the principles of the first embodiment of this invention.

As shown in FIG. 14, one of the guide wires of this invention can be used to navigate an endoscope 300 through a body lumen, such as a colon. The endoscope 300 has a lumen 302 extending therethrough. A magnetic field is applied to orient the magnet on the distal end of the guide wire with the magnetic field. The endoscope 300 can then be advanced over the guide wire, the lumen 302 sliding over the guide wire. The guide wire is preferably incrementally advanced, and the endoscope is then advanced over the guide wire, until the distal end of the endoscope 300 reaches its desired location.

Figure 15:
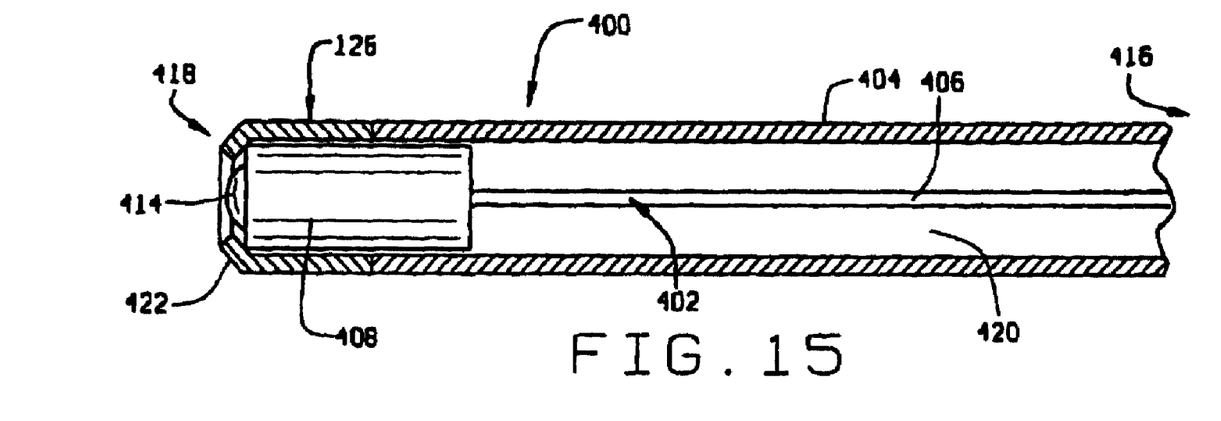
FIG. 15 is a longitudinal cross-sectional view of a guide wire and catheter combination according a second embodiment of this invention.
Figure 16:
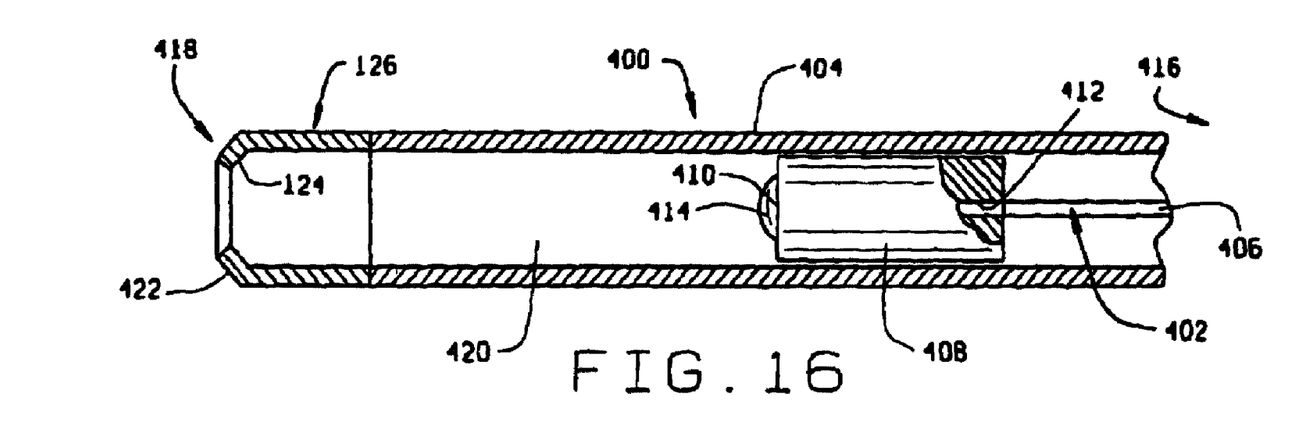
FIG. 16 is a longitudinal cross-sectional view of a guide wire and catheter combination with the guide wire partially withdrawn from the lumen of the catheter.

A guide wire and catheter combination constructed according to a second embodiment of this invention is indicated generally as 400 in FIGS. 15 and 16. The guide wire and catheter combination 400 comprises guide wire 402 and catheter 404. The guide wire 402 comprises a wire 406, preferably made of nitinol, which is highly flexible and resists kinking, although the guide wire could be made of some other suitable material. A magnet 408 is mounted on the distal end 410 of the wire 406. This magnet may either be a permanent magnet or a permeable magnetic material. A permanent magnet is easier to orient under the application of a magnetic field, as described below, but a permeable magnetic material is easier to pull under the application of a magnetic field.

In the preferred embodiment, the magnet 408 is made of NdFeB (neodymium-iron-boron) or samarium cobalt and is sized to respond to the magnetic field that will be applied to move the guide wire 402 through the body lumen. The magnet 408 is preferably elongate so that it can orient the tip of the guide wire 402 in the presence of an applied magnetic field. Magnets of about 0.3 mm (0.02 inches) to about 0.7 mm (0.03 inches) in diameter, and about 1 mm (0.04 inches) to 1.5 mm (0.06 inches) long are sufficiently large for use in navigating a guide wire.

As shown in FIG. 16, the magnet is preferably a cylindrical body with an axial bore 412 therethrough. The distal end of the wire 410 extends through the bore 412, and is secured with a bead 414 of adhesive on the distal side of the magnet 408. The bead 414 also provides a rounded head on the distal end of the guide wire 402. Of course instead of magnet 408, the guide wire 402 could have a plurality of spaced magnets on the distal end portion similar to guide wire 160, described above, or the distal end portion of the guide wire could be made of a flexible magnetic material similar to guide wire 180.

The catheter 404 is preferably of conventional construction, having a proximal end 416, a distal end 418, and a lumen 420 extending therebetween. The catheter 404 can be made of polyurethane tubing, or some other suitable material. The size of the catheter 404 depends upon where in the body it will be introduced, and how it will be used. For example, for use in the blood vessels in the brain, the catheter might have an outside diameter of about 0.7 mm (0.13 inches), an inside diameter of about 0.6 mm (0.11 inches), and a length of about 2 m (6.5 feet).

The guide wire 402 is adapted to fit inside the lumen 420, and "dock" with the catheter 404. To facilitate this, the distal end of the lumen 420 has a restriction or stricture 422 for engaging the distal end of the guide wire 402. This restriction or stricture is preferably formed by a annular flange or ring provided on the distal end of the catheter, although it could be some other reduction in the lumen that can be engaged by the guide wire. The ring can be made of tantalum.

The guide wire and catheter combination 400 can be introduced into a body lumen, such as a blood vessel, and navigated to its desired position by the controlled application of magnetic fields. The application of a magnetic field allows the operator to steer the distal end of the guide wire 402 by orienting the distal end of the guide wire to the desired direction of travel. The guide wire 402 can be advanced using the magnetic field to pull the magnets on the distal end or the guide wire can be advanced by pushing the proximal end. As the guide wire 402 advances, the catheter 404 can be advanced.

Once the distal end 418 of the catheter 404 has been placed in its desired location, the guide wire 402 can be withdrawn through the lumen 420, and out the proximal end 416.

Figure 17:
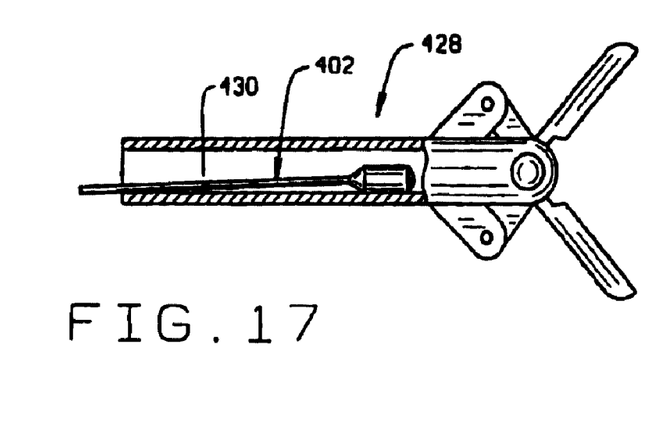
FIG. 17 is a side elevation view of a guide wire and biopsy device according to the principles of the present invention.

As shown in FIG. 17, the guide wire 412 can be used to navigate a biopsy tool 428 through a body lumen such as a kidney. The biopsy tool 428 has a lumen 430 therein. The distal end of the guide wire 402 is adapted to fit into the lumen 430 and "dock" with the biopsy tool. A magnetic field is applied to orient the magnet 408 inside the lumen 430 of the biopsy tool 428. The biopsy tool 428 can then be advanced, in the desired direction either by pushing the proximal end of the guide wire 402, or pulling the distal end of the guide wire with the magnetic field. When the biopsy tool 428 has been advanced to its desired location, the guide wire 402 can be withdrawn.

The guide wires of either embodiment can be used to deliver catheter or other medical devices to locations within the body accessible via a body lumen. For example the guide wire could be used to navigate a device for retrieval of man made objects e.g. stents, or body made objects e.g. stones. The high degree of articulation of the tip provides the control needed to capture and recover such objects.

Operation

In operation, one of the guide wires 22, 40, 50, 60, 70, 90, 110, 120, 130, 150, 160, or 180 of the first embodiment and an associated catheter or other medical device is introduced through a natural or surgically formed opening in a body lumen. A magnetic field is applied to orient the distal tip within the body lumen. The magnetic field can also be used to advance the distal tip of the guide wire, or the guide wire can be pushed to advance the guide wire in the body lumen. As the guide wire is incrementally advanced the catheter can be advanced over the guide wire. Once the distal end of the catheter is in its desired position, the magnet is removed from the catheter by pulling the guide wire to withdraw the magnet through the lumen of the catheter.

Because the magnet on the guide wire can be removed from the treatment site, multiple catheters can be directed in the same general area to facilitate a medical procedure with independent control of the catheters.

In operation, the guide wire 402 is inserted into the lumen of the catheter 404 (or other medical device) and the guide wire and catheter combination 400 of the second embodiment is introduced through an opening in a natural or surgically formed opening in a body lumen. A magnetic field is applied to orient the magnet 408 on the proximal end of the guide wire 402, inside the catheter 404. The guide wire and catheter are then advanced, either by applying a magnetic field, or by pushing the distal end of the guide wire. Once the distal end 418 of the catheter is in its desired position, the guide wire 402 is removed from the catheter 404 by pulling the guide wire 402 to withdraw it from the lumen 420 of the catheter.

Once the catheter 24 or 404 is in position it can be used for the administration of drug therapy or to perform a medical procedure or it can be used as a guide to insert medical devices to the area surrounding the distal end of the catheter to perform a medical procedure.

Because the magnet on the guide wire can be removed from the treatment site, multiple catheters can be directed in the same general area to facilitate a medical procedure with independent control of the catheters. Of course, the magnet could be left in place within the catheter, if desired.

What is claimed is:

1. A wire for use in navigating a medical device through a body lumen to a particular location, the guide wire having a proximal end and a distal end, and a magnet on the distal end, the guide wire being sufficiently flexible adjacent the magnet to allow the wire to flex in response to a magnetic field applied to the magnet, yet the wire being sufficiently stiff to allow the wire to be advanced through the body lumen;
   wherein the magnet on the distal end comprises a flexible magnetic material forming a distal end section of the guide wire.

2. In combination with a medical device having a proximal end, a distal end, and a lumen therebetween, a guide wire having a proximal end, a distal end, and a magnet on the distal end, the guide wire extending through the lumen of the medical device, with the distal end of the guide wire extending beyond the distal end of the medical device;
   wherein the magnet on the distal end comprises a flexible magnetic material forming a distal end section of the guide wire.

3. A method of navigating a medical device through a body lumen to a desired location within the body, the method comprising:
   providing a medical device having a lumen therethrough, the lumen having a proximal end and a distal end;
   inserting a guide wire having a proximal end and a magnetic distal tip, the distal tip of the guide wire being made from a flexible magnetic material, through the lumen of the device until at least a portion of the magnetic distal tip extends distally beyond the distal end of the lumen in the medical device;
   inserting the medical device and the guide wire into a lumen in the body;

navigating the medical device through the lumen in the body by applying a magnetic field to orient the magnetic tip in the desired direction of travel;

advancing the guide wire in the direction in which the magnetic tip is oriented; and advancing the medical device over the guide wire;

wherein the magnetic tip of the guide wire comprises a distal section of the guide wire being made from a flexible magnetic material.

4. The method according to claim 3, wherein the step of navigating the medical device comprises successively incrementally advancing the guide wire and the medical device.

5. A method of navigating a medical device through a body lumen to a desired location within the body, the method comprising:

providing a medical device having a lumen therethrough, the lumen having a proximal end and a distal end;

inserting a guide wire, having proximal end and a magnetic distal tip comprising a plurality of magnets secured on the distal end section of the guide wire in spaced apart relation allowing the guide wire to assume a shape under control of the magnetic field, through the lumen of the device until at least a portion of the magnetic distal tip extends distally beyond the distal end of the lumen in the medical device;

inserting the medical device and guide wire into a lumen in the body;

navigating the medical device through the lumen in the body by applying a magnetic field to shape the magnetic distal tip in the desired configuration to the orient the magnetic tip in the desired direction of travel;

advancing the guide wire in the direction in which the magnetic tip is oriented; and advancing the medical device over the guide wire.

6. The method according to claim 5, wherein the step of navigating the medical device comprises successively incrementally advancing the guide wire and the medical device.

7. In combination with a guide wire having a proximal end, a distal end, and a magnetic distal tip, a medical device having a proximal end, a distal end, and a lumen extending substantially to the distal end of the device, the guide wire extending into the lumen of the medical device with the magnetic distal tip in the distal end of the lumen in the medical device;

wherein a distal end portion of the guide wire is sufficiently flexible to allow the magnetic tip to move in response to an applied magnetic field, but a proximal section of the guide wire is sufficiently stiff to advance the medical device through a lumen in the body; and wherein the magnetic distal tip comprises a flexible magnetic material forming a distal end section of the guide wire.

8. The combination according to claim 7 wherein the lumen of the medical device has a stricture therein for engaging the guide wire and retaining the guide wire in the lumen of the medical device.

9. In combination with a guide wire having a proximal end, a distal end, and a magnetic distal tip, the magnetic distal tip comprises a plurality of magnets on the distal end section of the guide wire in spaced apart relation, the portion of the guide wire adjacent the distal end being sufficiently flexible to allow the magnetic tip to move in response to an applied magnetic field, but the proximal section of the guide wire being sufficiently stiff to advance a medical device through a lumen in the body, a medical device having proximal end, a distal end, and a lumen extending substantially to the distal end of the device, the guide wire extending into the lumen of the medical device with the magnetic distal tip in the distal end of the lumen in the medical device.

10. The combination according to claim 9 wherein the lumen of the medical device has a stricture therein for engaging the guide wire and retaining the guide wire in the lumen of the medical device.

11. A method of navigating a medical device through a body lumen to a desired location within the body, the method comprising:

providing a medical device having a proximal end; a distal end, and a lumen extending to substantially the distal end of the medical device;

inserting a guide wire having a proximal end and a magnetic distal tip into the lumen until the magnetic tip is substantially adjacent the distal end of the medical device, the magnetic tip of the guide wire comprises a plurality of magnets secured on the distal end section of the guide wire in spaced apart relation;

inserting the medical device and the guide wire into a lumen in the body;

navigating the medical device through the lumen in the body by applying a magnetic field to orient the magnetic tip inside the lumen of the medical device so that the distal end of the medical device is oriented in the desired direction of travel; and advancing the guide wire and medical device in the direction in which the distal end of the medical device is oriented.

12. The method according to claim 11 wherein the magnetic tip comprises a permeable magnetic material.

13. The method according to claim 11 wherein the magnetic tip comprises a permanent magnetic material.

14. The method according to claim 11, wherein the step of navigating the medical device comprises successively orienting and advancing the guide wire and medical device.

* * * * *